(12) United States Patent
Pulli et al.

(10) Patent No.: US 7,749,712 B2
(45) Date of Patent: Jul. 6, 2010

(54) NON-COMPETITIVE IMMUNOASSAY FOR SMALL ANALYTES

(75) Inventors: Timo Pulli, Helsinki (FI); Matti Hoyhtya, Helsinki (FI); Kristiina Takkinen, Espoo (FI); Hans Soderlund, Espoo (FI)

(73) Assignee: Valtion teknillinen tutkimuskeskus, Espoo (FI)

( * ) Notice: Subject to any disclaimer, the term of this patent is extended or adjusted under 35 U.S.C. 154(b) by 1190 days.

(21) Appl. No.: 10/535,260

(22) PCT Filed: Nov. 17, 2003

(86) PCT No.: PCT/FI03/00875

§ 371 (c)(1),
(2), (4) Date: May 18, 2005

(87) PCT Pub. No.: WO2004/046733

PCT Pub. Date: Jun. 3, 2004

(65) Prior Publication Data

US 2006/0246506 A1 Nov. 2, 2006

(30) Foreign Application Priority Data

Nov. 18, 2002 (FI) .................................. 20022048

(51) Int. Cl.
*G01N 33/00* (2006.01)
*G01N 33/53* (2006.01)
(52) U.S. Cl. ................ 435/7.1; 435/7.21; 436/501; 436/518; 530/300; 530/350
(58) Field of Classification Search .................. None
See application file for complete search history.

(56) References Cited

U.S. PATENT DOCUMENTS 5,223,441 A    6/1993   Ullman et al.
6,326,159 B1  12/2001   Ullman et al.

FOREIGN PATENT DOCUMENTS

| JP | 63112599 | 5/1988 |
| JP | 09154583 | 6/1997 |
| JP | 10507341 | 7/1998 |
| JP | 2001-174460 | 6/2001 |

OTHER PUBLICATIONS

Self et al. (Clinical Chemistry, vol. 40, No. 11, pp. 2035-2041, 1994).*
Arai et al. (Protein Engineering, vol. 13, No. 5, pp. 369-376, 2000).*
Yokozeki et al. (Analytical Chemistry A-E, 2002, vol. 74, pp. 2500-2504).*
Chan et al. (Cytometry, vol. 44, pp. 361-368, 2001).*
Barbas, C. et al., "Assembly of combinatorial antibody libraries on phage surfaces: The gene III site", *Proc. Natl Acad. Sci.*, vol. 88, pp. 7978-7982, Sep. 1991.
Hemmilä, I. et al., "Homogeneous time-resolved fluoroimmunossay of Thyroxin in serum", *Clinical Chemistry*, vol. 34, No. 11, 1988, p. 2320-2322.
Hoogenboom, H.R. et al., "Antibody phage display technology and its applications", *Immunotechnology* 4 (1998) 1-20.
Kobayashi, N. et al., "Monoclonal antibodies generated against an affinity-labeled immune complex of an anti-bile acid metabolite antibody: an approach to noncompetitive hapten immunoassays based on anti-idiotype or anti-metatype antibodies", *Journal of Immunological Methods*, 245 (2000) 95-108.
Kohler, G. et al., "Continuous cultures of fused cells secreting antibody of predefined specificity", *Nature*, vol. 256, Aug. 7, 1975, p. 495-497.
Mares, A. et al., "A direct non-competitive idiometric enzyme immunoassay for serum oestradiol", *Journal of Immunological Methods* 181 (1995) 83-90.
Maruyama, H. et al., "Immunization procedures for anti-idiotypic antibody induction in mice and rats", *Journal of Immunological Methods* 264 (2002) 121-133.
Arai et al., "Fluorolabeling of antibody variable domains with green fluorescent protein variants: application to an energy transfer-based homogenous immunoassay," *Protein Engineering*, vol. 13, No. 5, pp. 369-376, 2000.
Ullman, Edwin F. et al., "Anti-immune complex antibodies enhance affinity and specificity of primary antibodies", *Proc. Natl. Acad. Sci.*, vol. 90, Feb. 1993, pp. 1184-1189.
Little, M. et al., "Generation of a large complex antibody library from multiple donors", *Journal of Immunological Methods 231*, (1999) 3-9.
Tiivistelma Biosis PREV 198681092402, Immunological investigations, vol. 14 s. 523-540, Bolger et al., date 1985.
Tiivistelma Biosis PREV2002—8960, Biosensors & Bioelectronics, vol. 16, s. 639-646, Charlton et al., date 2001.
Self, C. et al., "High-performance assays of small molecules: Enhanced sensitivity, rapidity, and convenience demonstrated with a noncompetitive immunometric anti-immune complex assay system for digoxin", *Clinical Chemistry.*, vol. 40, No. 11, p. 2035-2041 (1994).
Suzuki, C. et al., "Open sandwich enzyme-linked immunosorbent assay for the quantitation of small haptens", *Analytical Biochemistry* 286, 238-246 (2000).

(Continued)

*Primary Examiner*—Lisa V Cook
(74) *Attorney, Agent, or Firm*—Young & Thompson (57) ABSTRACT

A non-competitive immunoassay for small analytes, wherein the analyte is reacted with two binding partners. The first binding partner binds to the analyte to form a complex between the first binding partner and the analyte, and the second binding partner binds to the complex formed by the first binding partner and the analyte. The resulting complex formed between the analyte and the binding partners is detected. The binding partners are proteins, such as antibodies including antibody fragments.

13 Claims, 3 Drawing Sheets

OTHER PUBLICATIONS

Suzuki, C. et al., "Open sandwich ELLISA with $V_H$-/$V_L$-alkaline phosphatase fusion proteins", *Journal of Immunological Methods*, 224 (1999) 171-184.

Szöllösi, J. et al., "Application of fluorescence resonance energy transfer in the clinical laboratory: routine and research", *Cytometry* 34: 159-179 (1998).

Towbin, H. et al., "Sandwich immunoassay for the hapten angiotensin II", *Journal of Immunological Methods* 181 167-176, date 1995.

Ueda, H. et al., "Open sandwich ELISA: A novel immunoassay based on the interchain interaction of antibody variable region", *Nature Biotechnology*, vol. 14, Dec. 1996, pp. 1714-1718.

Yokozeki, T. et al., "A homogeneous noncompetitive immunoassay for the detection for small haptens", *Analytical Chemistry*, A-E, date 2002.

Japanese Office Action in corresponding JP Application No. 2004-552756 dated Jul. 14, 2009.

* cited by examiner

SEQUENCE LISTING

```
<160> NUMBER OF SEQ ID NOS: 16

<210> SEQ ID NO 1
<211> LENGTH: 215
<212> TYPE: PRT
<213> ORGANISM: Mus sp.

<400> SEQUENCE: 1

Met Ala Asp Ile Lys Met Thr Gln Thr Pro Ser Ser Leu Ser Ala Ser
1               5                   10                  15

Leu Gly Asp Arg Val Thr Ile Ser Cys Arg Ala Ser Gln Asp Ile Ser
                20                  25                  30

Asn Tyr Leu Asn Trp Tyr Gln Gln Lys Pro Asp Gly Thr Val Lys Leu
            35                  40                  45

Leu Ile Tyr Tyr Thr Ser Arg Leu His Ser Gly Val Pro Ser Arg Phe
        50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Trp Thr Phe Gly Gly Gly Thr Lys Leu Glu Ile Lys Arg Ala Asp Thr
                100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
        130                 135                 140

Ile Asn Val Lys Trp Asn Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
210                 215
```

<210> SEQ ID NO 2
<211> LENGTH: 236
<212> TYPE: PRT
<213> ORGANISM: Mus sp.

<400> SEQUENCE: 2

Met Ala Ala Glu Val Lys Leu Val Glu Ser Gly Gly Thr Leu Val Lys
1               5                   10                  15

Pro Gly Gly Ser Leu Lys Leu Ser Cys Glu Ala Ser Gly Ile Thr Phe
            20                  25                  30

Ser Thr Tyr Val Met Ser Trp Val Arg Gln Thr Pro Glu Lys Arg Leu
        35                  40                  45

Glu Trp Val Ala Ser Ile Asn Ser Gly Gly Arg Thr Tyr Tyr Pro Asp
    50                  55                  60

Ser Val Lys Gly Arg Phe Ala Ile Ser Arg Asp Lys Gly Asn Ile
65                  70                  75                  80

Leu Tyr Leu Gln Leu Asn Ser Leu Arg Ser Glu Asp Thr Ala Ile Tyr
                85                  90                  95

Tyr Cys Ala Arg Glu Gly Ser Tyr Gly Asn Asn Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Val Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Thr Ser Trp Ser His Pro Gln Phe Glu Lys
225                 230                 235

<210> SEQ ID NO 3
<211> LENGTH: 215
<212> TYPE: PRT
<213> ORGANISM: Mus sp.

<400> SEQUENCE: 3

Met Ala Asp Ile Lys Met Thr Gln Thr Pro Ser Ser Leu Ser Ala Ser
1               5                   10                  15

Leu Gly Asp Arg Val Thr Ile Ser Cys Arg Ala Ser Gln Asp Ile Asn
            20                  25                  30

Tyr Tyr Leu Asn Trp Tyr Gln Gln Lys Pro Asp Gly Thr Val Lys Leu
        35                  40                  45

Leu Ile Tyr Tyr Thr Ser Ile Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Ala Leu
                85                  90                  95

```
Trp Thr Phe Gly Gly Gly Thr Lys Leu Glu Ile Lys Arg Ala Asp Ala
                100                 105                 110

Ala Pro Thr Val Ser Ile Phe Pro Pro Ser Ser Glu Gln Leu Thr Ser
            115                 120                 125

Gly Gly Ala Ser Val Val Cys Phe Leu Asn Asn Phe Tyr Pro Lys Asp
        130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215

<210> SEQ ID NO 4
<211> LENGTH: 236
<212> TYPE: PRT
<213> ORGANISM: Mus sp.

<400> SEQUENCE: 4

Met Ala Ala Glu Val Asn Leu Val Glu Ser Gly Gly Gly Leu Val Lys
1               5                   10                  15

Pro Gly Gly Ser Leu Lys Leu Ser Cys Glu Ala Ser Gly Ile Thr Phe
            20                  25                  30

Ser Lys Tyr Val Ile Thr Trp Val Arg Gln Ala Pro Glu Lys Arg Leu
        35                  40                  45

Glu Trp Val Thr Ser Ile Asn Ser Gly Gly Arg Thr Tyr Tyr Pro Asp
    50                  55                  60

Ser Val Lys Gly Arg Phe Ala Ile Ser Arg Asp Asn Ala Gly Asn Ile
65                  70                  75                  80

Leu Tyr Leu Gln Met Asn Ser Leu Arg Ser Glu Asp Thr Ala Ile Tyr
                85                  90                  95

Tyr Cys Thr Arg Glu Gly Ser Tyr Gly Asn Asn Trp Tyr Phe Asp Val
            100                 105                 110

Trp Gly Ala Gly Thr Thr Val Thr Leu Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Thr Ser Trp Ser His Pro Gln Phe Glu Lys
225                 230                 235
```

<210> SEQ ID NO 5
<211> LENGTH: 272
<212> TYPE: PRT
<213> ORGANISM: Homo sapiens

<400> SEQUENCE: 5

Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Thr Phe Asp
            20                  25                  30

Asp Tyr Ala Met His Trp Val Arg Gln Ala Pro Gly Lys Gly Leu Glu
        35                  40                  45

Trp Val Ser Gly Ile Ser Trp Asn Ser Gly Ser Ile Gly Tyr Ala Asp
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Arg Gly Gly Tyr Tyr Phe Asp Tyr Trp Gly Gln
            100                 105                 110

Gly Thr Leu Val Thr Val Ser Ser Leu Glu Gly Gly Gly Ser Gly
        115                 120                 125

Gly Gly Gly Ser Gly Gly Gly Ser Glu Leu Asp Ile Gln Met Thr
    130                 135                 140

Gln Ser Pro Ser Ser Leu Ser Ala Ser Val Gly Asp Arg Val Thr Ile
145                 150                 155                 160

Thr Cys Gln Ala Ser Gln Asp Ile Ser Asn Tyr Leu Asn Trp Tyr Gln
                165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
    210                 215                 220

Tyr Tyr Cys Gln Gln Ser Tyr Ser Thr Pro Tyr Thr Phe Gly Gln Gly
225                 230                 235                 240

Thr Arg Leu Glu Ile Lys Arg Ala Ala Ala Glu Gln Lys Leu Ile Ser
                245                 250                 255

Glu Glu Asp Leu Asn Gly Ala Ala Ser Arg His His His His His His
            260                 265                 270

<210> SEQ ID NO 6
<211> LENGTH: 106
<212> TYPE: PRT
<213> ORGANISM: Mus sp.

<400> SEQUENCE: 6

Asp Ile Lys Met Thr Gln Thr Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

-continued

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Trp Thr
                85                  90                  95

Phe Gly Gly Gly Thr Lys Leu Glu Ile Lys
            100                 105

<210> SEQ ID NO 7
<211> LENGTH: 107
<212> TYPE: PRT
<213> ORGANISM: Mus sp.

<400> SEQUENCE: 7

Arg Ala Asp Thr Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
                20                  25                  30

Tyr Pro Lys Asp Ile Asn Val Lys Trp Asn Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 8
<211> LENGTH: 120
<212> TYPE: PRT
<213> ORGANISM: Mus sp.

<400> SEQUENCE: 8

Glu Val Lys Leu Val Glu Ser Gly Gly Thr Leu Val Lys Pro Gly Gly
1               5                   10                  15

Ser Leu Lys Leu Ser Cys Glu Ala Ser Gly Ile Thr Phe Ser Thr Tyr
                20                  25                  30

Val Met Ser Trp Val Arg Gln Thr Pro Glu Lys Arg Leu Glu Trp Val
            35                  40                  45

Ala Ser Ile Asn Ser Gly Gly Arg Thr Tyr Tyr Pro Asp Ser Val Lys
        50                  55                  60

Gly Arg Phe Ala Ile Ser Arg Asp Asp Lys Gly Asn Ile Leu Tyr Leu
65                  70                  75                  80

Gln Leu Asn Ser Leu Arg Ser Glu Asp Thr Ala Ile Tyr Tyr Cys Ala
                85                  90                  95

Arg Glu Gly Ser Tyr Gly Asn Asn Trp Tyr Phe Asp Val Trp Gly Ala
            100                 105                 110

Gly Thr Thr Val Thr Val Ser Ser
        115                 120

<210> SEQ ID NO 9
<211> LENGTH: 103
<212> TYPE: PRT
<213> ORGANISM: Mus sp.

<400> SEQUENCE: 9

Ala Lys Thr Thr Pro Pro Ser Val Tyr Pro Leu Val Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly
            100

<210> SEQ ID NO 10
<211> LENGTH: 106
<212> TYPE: PRT
<213> ORGANISM: Mus sp.

<400> SEQUENCE: 10

Asp Ile Lys Met Thr Gln Thr Pro Ser Ser Leu Ser Ala Ser Leu Gly
1               5                   10                  15

Asp Arg Val Thr Ile Ser Cys Arg Ala Ser Gln Asp Ile Asn Tyr Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Ala Leu Trp Thr
                85                  90                  95

Phe Gly Gly Gly Thr Lys Leu Glu Ile Lys
            100                 105

<210> SEQ ID NO 11
<211> LENGTH: 107
<212> TYPE: PRT
<213> ORGANISM: Mus sp.

<400> SEQUENCE: 11

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 12
<211> LENGTH: 120
<212> TYPE: PRT
<213> ORGANISM: Mus sp.

<400> SEQUENCE: 12

Glu Val Asn Leu Val Glu Ser Gly Gly Gly Leu Val Lys Pro Gly Gly
1               5                   10                  15

Ser Leu Lys Leu Ser Cys Glu Ala Ser Gly Ile Thr Phe Ser Lys Tyr
            20                  25                  30

Val Ile Thr Trp Val Arg Gln Ala Pro Glu Lys Arg Leu Glu Trp Val
        35                  40                  45

Thr Ser Ile Asn Ser Gly Gly Arg Thr Tyr Tyr Pro Asp Ser Val Lys
    50                  55                  60

Gly Arg Phe Ala Ile Ser Arg Asp Asn Ala Gly Asn Ile Leu Tyr Leu
65                  70                  75                  80

Gln Met Asn Ser Leu Arg Ser Glu Asp Thr Ala Ile Tyr Tyr Cys Thr
                85                  90                  95

Arg Glu Gly Ser Tyr Gly Asn Asn Trp Tyr Phe Asp Val Trp Gly Ala
            100                 105                 110

Gly Thr Thr Val Thr Leu Ser Ser
        115                 120

<210> SEQ ID NO 13
<211> LENGTH: 103
<212> TYPE: PRT
<213> ORGANISM: Mus sp.

<400> SEQUENCE: 13

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly
            100

<210> SEQ ID NO 14
<211> LENGTH: 118
<212> TYPE: PRT
<213> ORGANISM: Homo sapiens

```
-continued

<400> SEQUENCE: 14

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Gly Tyr Tyr Phe Asp Tyr Trp Gly Gln Gly Thr
            100                 105                 110

Leu Val Thr Val Ser Ser
            115

<210> SEQ ID NO 15
<211> LENGTH: 19
<212> TYPE: PRT
<213> ORGANISM: Homo sapiens

<400> SEQUENCE: 15

Leu Glu Gly Gly Gly Gly Ser Gly Gly Gly Gly Ser Gly Gly Gly Gly
1               5                   10                  15

Ser Glu Leu

<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Tyr Ser Thr Pro Tyr
                85                  90                  95

Thr Phe Gly Gln Gly Thr Arg Leu Glu Ile Lys
            100                 105
```

NON-COMPETITIVE IMMUNOASSAY FOR SMALL ANALYTES

FIELD OF THE INVENTION

The present invention relates to immunoassays and especially to non-competitive immunoassays for small analytes. The present invention further relates to reagent pairs and test-kits useful in the assays, as well as to the use of the reagent pairs and to a process for their preparation. Novel reagents and means for their preparation are also provided.

TECHNICAL BACKGROUND OF THE INVENTION

In a competitive immunoassay, external reagent that competes with the analyte has to be added, which is not the case in the non-competitive assay format. The method of choice for the detection of analytes by immuno-chemistry is nowadays a non-competitive immunoassay, where two antibodies bind to two different epitopes of the analyte creating a so-called sandwich-type assay. Such an assay is well suited for high molecular weight analytes and it provides improved speed, sensitivity, and specificity, which are needed in modern immunoassays. However, it has been a difficult task to develop non-competitive assays for small analytes, because low molecular weight molecules are not large enough for binding simultaneously to more than one antibody independently. Therefore, despite many fundamental problems with respect to specificity and sensitivity, the competitive immunoassay format has been almost exclusively used for the detection of small analytes.

However, there are few publications where the development of a non-competitive immunoassay for a small analyte has been reported. In these papers, a secondary anti-immune complex (anti-IC) antibody, which binds primary anti-analyte antibody that is combined with the analyte but which does not bind the primary antibody or the analyte alone, has been developed (Ullman et al., 1993; Self et al., 1994; Towbin et al., 1995). Ullman et al., 1993, describe an antibody that recognizes an immune complex of an antibody to tetrahydrocannabinol (THC). The anti-IC antibody was obtained by using an affinity labelled anti-THC antibody as immunogen and selecting an anti-IC antibody the binding of which was enhanced by the presence of $\Delta^9$THC. Self et al., 1994, used the same principle in preparing anti-IC antibodies for determining digoxin. Towbin et al., 1995, report a sandwich immunoassay for the hapten angiotensin II, wherein the immunisation involves tolerization with uncomplexed primary antibody prior to immunisation with the anti-immune complex to obtain the anti-IC antibodies. The anti-IC antibodies used in non-competitive immunoassays for small analytes have so far been conventional polyclonal or monoclonal antibodies obtained by immunisation, and the assays described here include labelling of the primary antibody and immobilisation of the secondary or vice versa.

So-called 'idiometric' non-competitive immunoassay for small analytes has been developed by Mares et al., 1995. They used two types of anti-idiotypic antibodies, which recognize different epitopes within the hypervariable region of the oeastradiol specific primary antibody. The first anti-idiotypic antibody (betatype) possesses the capacity of competing with the analyte for an epitope at the binding site of the primary antibody. The second anti-idiotype (alphatype) recognizes an epitope within the variable region of the primary antibody and the binding is not sensitive to the presence of the analyte. The alphatype is, however, sterically hindered from binding to the primary antibody in the presence of the betatype. These three types of antibodies permit the development of a non-competitive assay for small analytes.

So-called open sandwich immunoassays have been developed for the detection of haptens (Suzuki et al., 2000; Suzuki et al., 1999; Yokozeki et al., 2002). They are non-competitive assays based on a phenomenon according to which the association of separated $V_H$ and $V_L$ chains in some antibodies is strongly favoured in the presence of antigen (Ueda et al., 1996).

Despite the significant benefits of the non-competitive immunoassay format, only few examples of that kind of assays for small analytes have been reported. The reason for that is most probably the difficulty of producing secondary (anti-immuno complex, or anti-idiotypic) antibodies by immunising animals. For example anti-hapten monoclonal antibodies, which have been developed by hybridoma technology (Kohler and Milstein, 1975), are self-antigens for mice and raising immunoresponse against them is difficult (Maruyama et al., 2002; Ullman et al., 1993; Kobayashi et al., 2000). A further problem is that the immune complex used for immunisation tends to break down before the response to the immuno complex is obtained (Ullman et al., 1993; Kobayashi et al., 2000).

The present invention now provides a non-competitive immunoassay protocol for small analytes, which circumvents the immunisation of animals with the immune complex, which has been so far the most challenging task when anti-IC antibodies have been developed. The invention also facilitates a homogenous immunoassay, which further improves the speed, sensitivity and simplicity of the assay.

SUMMARY OF THE INVENTION

The difficulties associated with raising anti-IC antibodies for use in immunoassays for small analytes can now be avoided by providing the necessary anti-IC antibodies from a display recombinant binding partner library instead of from immunised animals. A phage display antibody library may be constructed, which contains a vast number of clones, from which those coding the desired binding partners, such as antibody fragments, can be enriched and selected through sequential panning. This protocol opens new possibilities for developing rapid, reliable and simple immunoassays for small analytes in a cost-effective and feasible way.

Consequently, one object of the present invention is a non-competitive immunoassay for a small analyte comprising reacting a sample containing said analyte with a reagent pair comprising a first binding partner that binds to said analyte, and a second binding partner that binds to the complex of said analyte and said first binding partner. The immunoassay is characterized in that the second binding partner is obtained from a display recombinant binding partner library by selecting a binding partner that binds to said complex of the analyte and first binding partner, and determining the binding of the second binding partner thus indicating the presence of the analyte in the sample.

Another object of the invention is a reagent pair for a non-competitive immunoassay for a small analyte, comprising a first binding partner that binds to said analyte, and a second binding partner that binds to the complex of said analyte and said first binding partner, characterized in that the second binding partner is obtained from a display recombinant binding partner library by selecting a binding partner that binds to said complex of the analyte and first binding partner.

Still another object of the present invention is a test kit for a non-competitive immunoassay for a small analyte, said kit comprising a reagent pair comprising a first binding partner that binds to said analyte, and a second binding partner that binds to the complex of said analyte and said first binding partner, characterized in that the second binding partner is obtained from a display recombinant binding partner library by selecting a binding partner that binds to said complex of the analyte and first binding partner.

The invention is also directed to the use of a reagent pair comprising a first binding partner that binds to an analyte, and a second binding partner that binds to the complex of said analyte and said first binding partner, in a non-competitive immunoassay for a small analyte, whereby the second binding partner is obtained from a display recombinant binding partner library by selecting a binding partner that binds to said complex of the analyte and first binding partner.

A still further object of the invention is a process for preparing a reagent pair for a non-competitive immunoassay for a small analyte comprising providing a first binding partner that binds to said analyte, and a second binding partner that binds to the complex of said analyte and said first binding partner, characterized in that the second binding partner is obtained from a display recombinant binding partner library by selecting a binding partner that binds to said complex of the analyte and first binding partner.

The invention also provides novel recombinant binding proteins, characterized in that they comprise the ligand-binding portion of M1 Fab comprising SEQ ID NO 1 and SEQ ID NO 2; M2 Fab comprising SEQ ID NO 3 and SEQ ID NO 4; or K11 scFv comprising SEQ ID NO 5.

DNA encoding the novel binding proteins as well as host cells expressing them are also included in the invention.

Advantagous embodiments of the invention are set forth in the dependent claims.

Other objects, details and advantages of the present invention will become apparent from the following drawings, detailed description and examples.

BRIEF DESCRIPTION OF THE DRAWINGS

FIG. 2. A non-competitive time resolved fluorescent immunoassay (TR-FIA) with the Eu labelled anti-M1+ morphine immune complex scFv fragment K11. a) Cross-reactivity and sensitivity of the assay. b) Sensitivity of the assay with S1 urine control dilutions as samples.

DETAILED DESCRIPTION OF THE INVENTION

The reagent pair for the non-competitive immunoassay of the invention comprises a first binding partner and a second binding partner. The first binding partner binds to the analyte to form a complex between the first binding partner and the analyte. The second binding partner binds to the complex formed by the first binding partner and the analyte. The binding partners are usually proteins such as antibodies including antibody fragments that have the desired binding properties. An antibody is an immunoglobulin molecule and it can belong to any of classes IgG, IgM, IgE, IgA or IgD; IgG and IgM being the most frequently used. Preferably the binding partners are antibody fragments comprising the ligand-binding site, such as Fab, or scFv fragments. The fragment known as the Fab fragment (fragment antigen binding) consists of the variable and constant domain of an immunoglobulin light chain covalently attached by a disulfide bridge to the variable and first constant domain of an immunoglobulin heavy chain. Fv (variable domain) means the variable regions of the immunoglobulin molecule that are responsible for the ligand binding. ScFv (single chain Fv) means a molecule wherein the variable domains of the heavy and light chain of an antibody are linked by a peptide to form a single polypeptide chain synthesized from a single mRNA molecule. The variable regions of an immunoglobulin heavy chain and light chain are together responsible for the ligand binding. Ligand is the substance to which the binding partner binds, in connection with antibodies it is an antigen or a hapten.

The first binding partner may be a conventional polyclonal or monoclonal antibody or fragment thereof, but preferably it is a recombinant one, as is the second binding partner. When the first binding partner has been selected for, it is complexed with its ligand and this complex is used to select for the second binding partner from a recombinant library. The first binding partner without the ligand is used as contraselection. The second binding partner should only recognise complexes, not free first binding partner nor free antigen to any significant extent.

The recombinant binding partner library is conveniently an expression library, which is typically a display library. The general principle of the display recombinant binding partner libraries is that they present the binding partner as a fusion protein on the surface, which may be the surface of a microbial cell such as a yeast or bacterial cell, or a phage. The display recombinant binding partner library can also be a display library, where stable complexes of nascent protein and mRNA are produced in an in vitro expression system. Phage display libraries are the most frequently used. Antibody phage display technology and its applications are described e.g. in Hoogenboom et al., 1998.

A phage display antibody library may be constructed by cloning immunoglobulin domains coding cDNAs into an appropriate phage display vector. DNA encoding for millions of variants of antibody fragments is batch-cloned into the vector as part of the phage coat protein. Large libraries containing millions of antibody fragments with different specificities can be obtained by transforming the vectors in bacteria. Cultivation of the bacteria leads to the expression of phages displaying antibody fragments on their surface. The gene for the displayed antibody is carried in the phage genome, thus linking genotype with phenotype. The physical linkage between the displayed protein and its DNA allows screening of vast numbers of variants of the protein, each linked to its corresponding DNA, by a simple in vitro selection procedure called panning. In its simplest form, panning is carried out by incubating the pool of phage-displayed variants with the ligand of interest that has been immobilized on a carrier, washing away unbound phage, and eluting specifically bound phage by disrupting the binding to the ligand. The eluted phage is then amplified in vivo. The process is repeated several times, resulting in stepwise enrichment of the phage pool in favour of the tightest binding sequences. After about 3 to 6 rounds of selection and amplification, the best clones are sequenced and transformed into a host cell for further expression. The host cell may be a eucaryotic or procaryotic cell e.g. a yeast, animal, plant or insect cell or bacterial cell. It may even be a hybridoma cell, which after transformation produces a recombinant monoclonal antibody. The recombinant binding partner or at least part of it may also be produced synthetically.

The concept to use recombinant antibody libraries makes the non-competitive sandwich assay for small analytes feasible. The sandwich can be detected by all the standard immunoassays. Usually one partner is immobilized on a carrier, such as a microtiter well or a bead. A sandwich is formed in the presence of analyte and the other binding partner. The sandwich may be detected e.g. by using secondary antibodies or by labelling at least one of the binding partners. The label can be any conventional label, such as a radioactive label, an enzyme, or a fluorescent compound. The assay can be e.g. ELISA or FIA.

A great advantage of the reagent pair of the present invention is that it enables a homogenous non-competitive immunoassay, i.e. an immunoassay that is carried out in solution. The avoidance of immobilising and washing steps makes the assay extremely simple. Such a test is also suitable for testing on-site i.e. in places elsewhere than the laboratory.

A preferred homogenous immunoassay is one based on fluorescence resonance energy transfer (FRET), for review see Szollosi et al., 1998. In FRET, energy from a molecular fluorophore (donor) is excited to a high-energy state and transferred to another fluorophore (acceptor) via intermolecular dipole-dipole coupling. This is possible only if the distance between the donor and the acceptor is short (10-100 Å) and the fluorescence spectrum of the donor and the absorption spectrum of the acceptor partially overlap. The energy transfer is then detected as a change in fluorescence. Often time-resolved fluorescence is utilized (Hemmila et al., 1988).

FRET is applied to the present invention by labelling the two binding partners, which preferably are antibody fragments, with fluorophores that form a FRET donor-acceptor pair. When the binding partners and the analyte are small the fluorophores come into very close proximity, and a measurable FRET signal is obtained.

The invention provides a convenient and rapid analytical tool for low molecular weight analytes, such as therapeutic and abused drugs, steroids, hormones, metabolites, and environmental pollutants and toxins. A common feature of these small analytes is that they are too small for conventional sandwich assays where two antibodies recognizing different epitopes of the antigen are used. The molecular weight of these small analytes are normally less than 5000, but the limits are not absolute.

The immunoassay may be employed in all kinds of investigations, such as in detecting environmental hazards, toxic compounds in food and feed, chemicals indicative of ongoing processes e.g. of microbial processes in buildings, metabolic processes of living organisms, and in clinical tests, drug monitoring and pharmacological research. The assays are extremely suitable for detecting drugs of abuse, such as opiates (e.g. morphine), amphetamines, cannabinoids (e.g. tetrahydrocannabinol (THC)), barbiturates, benzodiazepines, cocaine, LSD, methadone, methaqualone, phencyclidine, propoxyphene, tricyclic antidepressants. The homogenous assay provides an excellent and convenient tool for on-site tests e.g. to be used by the police in raiding drivers etc. The sample to be analysed for e.g. drugs and abused drugs may be any body fluid sample, such as blood, serum, urine or saliva.

The reagent pair of the invention may be included in a test-kit. This test-kit may further comprise any other reagents needed for the assay, such as reaction solutions, buffers, washing solutions and detecting means, such as labels and optionally a fluorometer. Preferably the test-kit comprises multiple reagent pairs physically separated from each other, e.g. many in the form of a microarray, whereby e.g. many different drugs of abuse may be tested simultaneously from a single saliva sample.

In a special embodiment of the invention, a reagent pair for detecting morphine is produced and employed in a homogenous immunoassay for said substance. The first binding partner is a Fab fragment obtained from a phage display antibody library produced from cDNA from a mouse immunized with morphine conjugated to an immunocarrier BSA. Morphine specific antibody phages were enriched by selecting those binding to morphine conjugated BSA and sorting out those binding to BSA alone. After several panning rounds two high binding clones are sequenced and expressed. The expressed Fab fragments were named M1 Fab and M2 Fab.

The second binding partner is obtained from a naive scFv antibody fragment phage display library by selecting antibodies that bind to a complex of morphine and M1 Fab. First the phages are preincubated to bound M1 Fab to sort out those binding to M1 Fab as such. The unbound phages are separated and incubated with a mixture of morphine and immobilised M1 Fab to select the phages that bind to the immunocomplex formed between the immobilized M1 Fab and morphine. Unbound phages are washed away, and then those bound to the complex are eluted. The background is monitored by checking the binding to M1 Fab in the absence of morphine. After several panning rounds a number of clones are picked up, sequenced and expressed resulting in scFv fragment K11.

A fluorescence-based immunoassay is performed using M1 Fab labelled with europium as a first binding partner, and scFv fragment K11 labelled with Cy5 as a second binding partner. The binding partners are incubated with saliva or urine samples containing morphine and then fluorescence is measured after a predetermined time. The assay is completely homogeneous and the signal is readable in about 5 min. The sensitivity for both urine and saliva is clearly higher than that demanded by the authorities in the case of morphine, our model analyte. The performance of the test is such that the reagents are in the well of a microtiter plate and dilution series of either saliva or urine is added. In a preferred mode for e.g. police field use, the reagents are in dry form in a vessel. Saliva is added, which dissolves the reagents and the result can be read without further processes.

The novel recombinant binding proteins provided by the invention comprise any ligand-binding portion of M1 Fab, M2 Fab or K11 scFv. By "ligand-binding portion" is meant that part of the molecule that is responsible for the binding. Minor variations or modifications of the sequences set forth in the description and claims are still within the scope of the invention provided that they do not affect the binding activity of the proteins.

The invention is illustrated by the following non-limiting example. It should be understood, however, that the embodiments given in the description above and in the examples are for illustrative purposes only, and that various changes and modifications are possible within the scope of the invention.

EXAMPLE 1

Development of an Anti-morphine Antibody

Immunisation of Mice

Four six-week-old female Balb/c mice were immunised in three-week intervals with morphine conjugated BSA (Fitzgerald) in Freund's adjuvant. Serum samples were tested after second booster and the mouse showing the best response against the antigen in direct ELISA was selected to be the source of an antibody phage display library.

Construction of the Antibody Phage Display Library

All basic recombinant DNA methods were performed essentially as described (Sambrook et al. 1990). The mouse with the highest antibody response to morphine-BSA conjugate was sacrificed and the total RNA was isolated from the spleen cells using the RNagentse Total RNA Isolation System (Promega Co., WI, USA). The mRNA pool of the total RNA was isolated with the Oligotex mRNA Kit (QIAGEN Inc., Germany). The cDNA was synthesised from the mRNA with oligo-dT priming. Genes encoding antibody Fab fragments were amplified with PCR using antibody kappa light chain and heavy chain variable region and constant region specific primers. Antibody light chain PCR products were pooled and digested with NheI and AscI restriction enzymes, purified by preparative agarose gel in combination with the QIAquick Gel Extraction Kit (QIAGEN Inc., Germany). The agarose gel purified antibody light chain DNA was ligated into the Fab phagemid vector phagemid9 derived from pComb3 (Barbas et al., 1991) and transformed into the *E.coli* XL1-Blue strain (Stratagene) by electroporation. Plasmid DNA was isolated with the QIAGEN Plasmid Midi Kit (QIAGEN Inc., Germany) from the overnight culture. PCR products encoding the Fd region (variable and first constant region) of the heavy chain were pooled and digested with SfiI and NotI restriction enzymes, purified by preparative agarose gel isolation and ligated to the phagemid vector containing the light chain DNA. The phagemid vector encoding both the heavy and light chain of the Fab fragment was transformed into the *E.coli* TOP10F' bacteria (Invitrogen Inc., CA, USA) by electroporation. Transformed bacteria were incubated over night at +37° C. on a shaker and plasmid DNA was isolated with the QIAGEN Plasmid Midi Kit. The diversity of the antibody library was ensured by sequencing partial $V_L$- or $V_H$-gene regions of individual clones.

A phage display antibody library was made as follows: 4 µg of antibody library plasmid DNA was transformed into *Ecoli* TOP10F' by electroporation in two parallel transformations. After transformations, cells were suspended into 2.8 ml of SOC medium and incubated for 1 h at +35° C. on a shaker. 7 ml of prewarmed (+37° C.) SB medium, 20 µg/ml of carbenicillin, and 10 µg/ml of tetracycline was added. After 1-h incubation at +35° C. on a shaker, 30 µg/ml of carbenicillin was added and the incubation was continued for 1 h after which 1 ml (~$10^{11}$ pfu) of helper phage VCS-M13 (Stratagene) was added and the phages were let to infect the bacteria for 20 min at +35° C. with a slow shaking. The parallel transformations were joined together and 80 ml of prewarmed (+37° C.) SB medium with 50 µg/ml carbenicillin and 10 µg/ml of tetra-cycline was added. After 2-h incubation at +35° C. on a shaker, 70 µg/ml of kanamycin was added and the incubation was continued over night.

Cells were centrifuged for 15 min at 4000 g at +4° C. 20 ml of 20% PEG, 2.5 M NaCl (PEG/NaCl) was added to the supernatant and it was incubated for 30 min on ice. PEG precipitated phages were centrifuged for 20 min at 13000 g at +4° C. The pellet was suspended in 2 ml of PBS and 1 ml was transferred into two eppendorf tubes. After centrifugation for 5 min at +4° C., phages were precipitated by adding 200 µl of PEG/NaCl to the supernatant. The solution was mixed and centrifuged for 5 min at +4° C. The pellet was suspended in 1 ml of PBS or PBS+1% BSA. 1 µl of 20% Na-azide was added as a preservative. The phage display antibody library was stored at +4° C.

Selection of the Anti-Morphine Library

Morphine specific antibodies were selected from the phage display antibody library by the following selection procedure: A microtiter well was coated over night at +4° C. with 1 µg of morphine conjugated BSA (morphine-BSA; Fitzgerald Industries International, Inc., MA, USA) in 100 µl of 100 mM Na-bicarbonate buffer, pH 9.8. The well was washed two times with PBS and blocked with 1% BSA in PBS for 1 h at +37° C. 100 µl of the phage library was incubated in the well for 1 h at RT with shaking, after which the unbound phages were removed and the well was washed 22 times with PBS. Bound phages were eluted with 100 µl of 100 mM HCl (pH 2.2) for 15 min. Eluted phages were removed from the well and neutralised with 1 M Tris. 3 ml of fresh *E.coli* XL1-Blue cells ($OD_{600} \approx 1$) grown in SB supplemented with 10 µg/ml of tetracycline was infected with eluted phages at +35° C. for 15 min. 7 ml of prewarmed SB (+37° C.) with 20 µg/ml of carbenicillin and 10 µg/ml of tetracycline was added and the culture was incubated for 1 h at +35° C. on a shaker. 30 µg/ml of carbenicillin was added and incubation was continued for 1 h. 1 ml of helper phage VCS-M13 was added to the culture and incubated at +35° C. for 15 min with a slow shaking. The culture was diluted with 90 ml of prewarmed (+37° C.) SB with 50 µg/ml carbenicillin and 10 µg/ml tetracycline. After 2 h incubation at +35° C. on a shaker, 70 µg/ml of kanamycin was added and the incubation was continued over night. The purification of the amplified phages was performed by PEG precipitation as described above.

The purified phages were used in further enrichment rounds. After four selection rounds, morphine specific antibody phages had been enriched over 1000 times when compared to the background. The background binding of the phages was monitored in parallel in each selection round by incubating the phage library in a BSA coated microtiter well. The well was washed and the phages were eluted as in the morphine-BSA coated well. The enrichment of the morphine specific phages was monitored by comparing the amount of the eluted phages from the morphine-BSA coated well to the amount of eluted phages from the background well.

Characterisation of Individual Clones

After the fourth panning round, the phagemid DNA was isolated with the QIAGEN Plasmid Midi Kit. The plasmid was digested with NheI and NotI restriction enzymes to isolate the Fab gene fragment. The agarose gel isolated DNA was ligated to the expression vector pKKtac. The ligation reaction was transformed into the *E.coli* XL1-Blue cells.

Individual clones were picked and miniprep DNA was extracted with the QIAprep Spin Miniprep Kit (QIAGEN Inc., Germany). According to sequencing of the minipreps, two different Fab clones were found. These clones were named M1 and M2. The amino acid sequences of the M1 Fab fragment were SEQ ID NO 1 (light chain) and SEQ ID NO 2 (heavy chain). Amino acids no. 3 to 108 (SEQ ID NO 6) represent the variable region and no. 109 to 215 (SEQ ID NO 7) the constant region of the M1 light chain (SEQ ID NO 1). Amino acids no 4 to 123 (SEQ ID NO 8) represent the variable region and no. 124 to 226 (SEQ ID NO 9) the constant region of the M1 heavy chain (SEQ ID NO 2) The amino acid sequences of M2 Fab fragment were SEQ ID NO 3 (light chain) and the SEQ ID NO 4 (heavy chain). Amino acids no. 3 to 108 (SEQ ID NO 10) represent the variable region and no. 109 to 215 (SEQ ID NO 11) the constant region of the M2 light chain (SEQ ID NO 3). Amino acids no. 4 to 123 (SEQ ID NO 12) represent the variable region and no. 124 to 226 (SEQ ID NO 13) the constant region of the M2 heavy chain (SEQ ID NO 4). The rest of the amino acids derive fro the cloning technique, and some of the C-terminal amino acids facilitate the isolation and purification of the protein. Small-scale (3 ml) Fab expression cultures were also made. Periplasmic fraction of the cells was isolated by freezing and thawing the cells for three times in PBS.

The binding of individual Fab clones to morphine was tested by ELISA in morphine-BSA coated microtiter wells: Microtiter wells were coated with 200 ng of morphine-BSA in 0.1 M Na-bicarbonate buffer, pH 9.8 for over night at +4° C. Control wells were filled only with the buffer. After coating, wells were washed three times with PBS and blocked with 0.5% BSA in PBS (BSA/PBS) for 1 h at RT. Wells were washed three times with PBS and 1:10 dilution of the periplasmic fractions was added into wells in 100 µl of BSA/PBS. After 1-h incubation at RT on a shaker, wells were washed three times with PBS and 1:2000 diluted alkaline phosphatase conjugated anti-mouse Fab specific antibody (Sigma, A-1293) was added in 100 µl of BSA/PBS. The wells were incubated for 1 h at RT on a shaker and washed three times with PBS. 100 µl of alkaline phosphatase substrate solution (2 mg/ml of p-nitrophenylphosphate di-Na-salt in diethanolamine-MgCl-buffer) was added to the wells and absorbance was measured. According to the preliminary results, the M1 Fab showed better performance in the assay and was therefore chosen for the continuation.

Fermentation and Purification

The anti-morphine Fab fragment M1 in the expression vector pKKtac was transformed in the E. coil expression strain RV308. The Fab was expressed by fed-batch fermentation in a Bio-Flow IV fermenter (New Brunswick) and purified by the SEPHAROSE SP ion-exchange and protein G chromatography (Pharmacia).

Performance of the Primary Antibody in a Competitive Immunoassay

Figure 1:
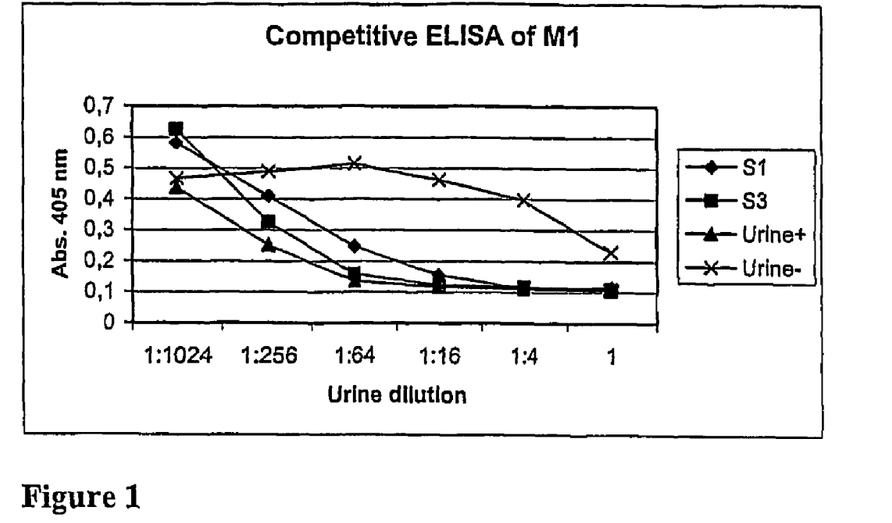
FIG. 1. A competitive ELISA using M1 Fab. Urine+ is urine spiked with 1 μg/ml of morphine.

The performance of the M1 anti-morphine Fab fragment was tested in a competitive ELISA assay using the commercial urine toxicology controls S1 and S3 (Bio-Rad). The S1 urine toxicology control contains drugs and drug metabolites (including morphine) at concentrations 20-25% below immunoassay cut-off levels as recommended by the U.S. Substance Abuse and Mental Health Services Administration (SAMSHA) and other agencies. The S3 urine toxicology control contains drugs and drug metabolites at concentrations approximately three times immunoassay cut-off levels. Microtiter wells were coated over night at +4° C. with 500 ng of morphine-BSA in 100 µl of Nabicarbonate buffer, pH 9.8. Wells were washed three times with PBS and blocked with BSA/PBS for 1 h at RT. After three washes with PBS, S1, S3 (Bio-Rad), positive control, or negative control urine dilutions were added to the wells in 100 µl of BSA/PBS spiked with 1 ng of M1 Fab. Wells were incubated for 2 h at RT on a shaker and washed three times with PBS. 1:2000 diluted alkaline phosphatase conjugated anti-Fab antibody (Sigma, A-1293) was added to the wells in 100 µl of BSA/PBS and incubated for 1 h at RT on a shaker. Wells were washed three times with PBS, 100 µl of alkaline phosphatase substrate solution was added and $A_{405}$ was measured. Results are shown in FIG. 1. A positive result could be achieved with 1:64 dilution of the sample.

Development of an Anti-immune Complex Antibody Specific to the Immune Complex of M1 Fab and Morphine Selection of the Immune Complex Specific Antibody from a Naive Human scFv Phage Display Library M1 Fab fragment was biotinylated with ImmunoPure Sulfo-NHS-LC-Biotin Kit (Pierce). Biotinylated antibody was purified and buffer was changed to PBS with Econo-Pac 10DG Columns (Bio-Rad, CA, USA). 200 µl of a naive human scFv phage display library (Kappa or Lambda light chain) in BSA/PBS was preincubated with 10 µl of streptavidin coated magnetic beads (Dynal, M-280) and 0.5 µg of biotinylated M1 Fab for over night at +4° C. The naive human scFv phage display library was constructed from pooled lymphocytes of 50 healthy individuals. The size of the library was estimated to be $1 \times 10^8$ clones. The naive human scFv phage display library contains the IgM specific $V_H$-genes combined either with the kappa or lambda specific $V_L$-genes. Unbound phages were separated from the beads and 100 µl of them was incubated with 100 ng of morphine, 500 ng of biotinylated M1 Fab, and 5 µl of streptavidin coated magnetic beads for 1 h at RT on a shaker. The background for the selection procedure was implemented in a similar way but omitting the morphine from the binding reaction. Magnetic beads were washed five times with 0.5 ml of PBS and bound phages were eluted with 100 µl of HCl (pH 2.2) for 30 min. The eluted phages were neutralised with 1M Tris and E.coli XL1-Blue cells were infected. Cells were grown and phages were purified as described previously. After five panning rounds enrichment was seen with the scFv library having the kappa light chains, when the amount of eluted phages was compared to the amount of eluted phages from the background control well. The enrichment of specific binders to the immune complex, formed by M1 Fab and morphine, was also clearly seen in a phage ELISA when the eluted phage pools from the selection rounds were tested.

Characterisation of Individual Clones

Individual phage clones were picked and they were sequenced. All of the clones had the same sequence (SEQ ID NO 5) The amino acid sequence of anti-M1+ morphine immune complex scFv fragment was named K11 scFv. Amino acids no. 3 to 120 (SEQ ID NO 14) represent the heavy chain variable region, no. 140 to 246 (SEQ ID NO 16) represent the light chain variable region, and no. 121 to 139 (SEQ ID NO 15) represent the linker of K11 scFv (SEQ ID NO 5). The rest of the amino acids derive from the cloning technique, and some of the C-terminal amino acids facilitate the isolation and purification of the protein.

Expression and Purification

The gene encoding the scFv fragment K 11 was inserted into the 5 expression vector pKKtac and transformed into the E.coli RV308 strain. Cells were inoculated into 20 ml of LB with 100 µg/ml ampicillin and were incubated over night at +37° C. on a shaker. From the overnight culture a 10 ml inoculate was added into two erlenmeyer bottles containing 500 ml of LB with 100 µg/ml of ampicillin. Cells were incubated at +37° C. on a shaker until the $OD_{600}$ was 1 after which 0.5 ml of 1M IPTG and 100 µg/ml of ampicillin were added into the culture and the incubation was continued over night at +30° C. on a shaker. Both the supernatant of the culture medium and the periplasmic fraction of the cells were used for the purification of the K11 scFv. Cells were centrifuged at 4000 g for 15 min and the supernatant was poured into a clean flask. The cells 1.5 were resuspended in 20 ml of PBS. The periplasmic fraction of the cells was isolated by freezing (−70° C.) and thawing (+37° C.) the cells for three times. After centrifugation at 12000 g for 30 min, the clear periplasmic supernatant was taken. The culture medium and the periplasmic fraction were treated with 2 mg/ml of DNaseI to remove residual chromosomal DNA for two hours at +37° C. Since the expressed K11 scFv has a 6×His-tag in its C-terminus, it could be purified by immobilised metal affinity chromatography (IMAC). The K11 scFv was purified by expanded bed chromatography using STREAMLINE Chelating (Amershampharmacia biotech) as a matrix and copper as the metal chelate. The purity of K11 scFv was checked with SDS-PAGE.

Development of a Non-competitive Immunoassay for Morphine

Labelling of the Anti-Immune Complex Antibody K11 scFv with Europium

The purified anti-M1 and morphine immune complex scFv fragment K11 was labelled with europium chelate by the DELFIA Eu-Labelling Kit (Wallac) as described by the manufacturer. Buffer of the labelled K11 scFv was changed to 50 mM Tris pH 7.8, 0.9% NaCl. Labelling yield was 0.4 Eu/scFv.

A Non-competitive Immunoassay for Morphine

Figure 2A:
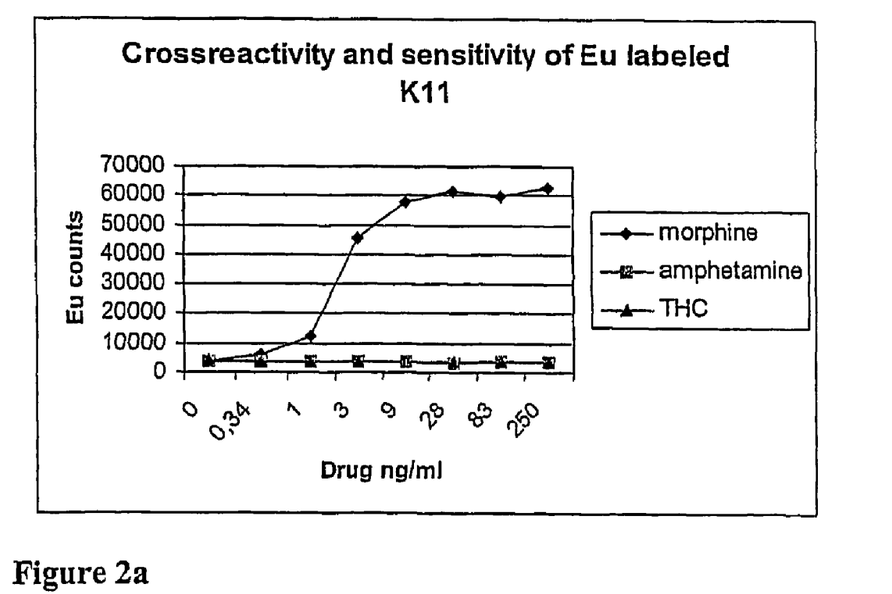
Figure 2B:
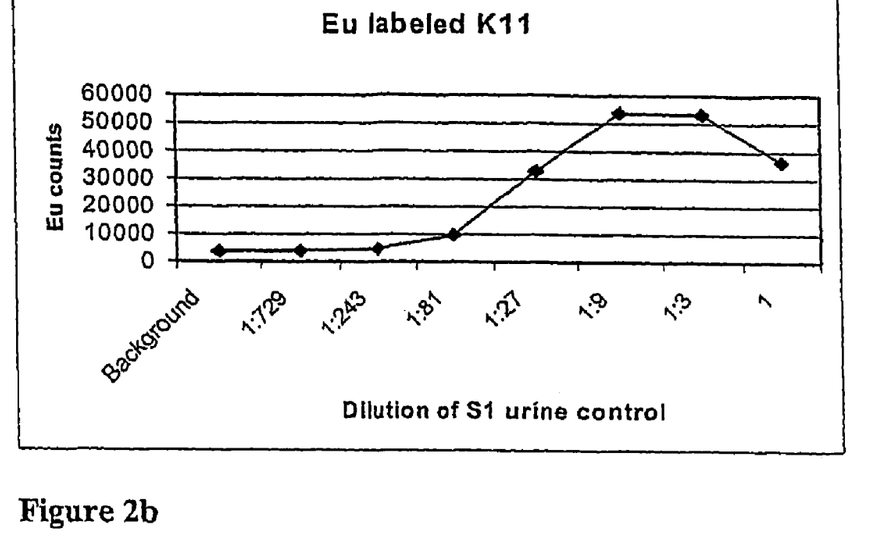

The sensitivity and cross-reactivity of K11 scFv was studied by a non-competitive immunoassay. Transparent Streptawell (Roche) streptavidin coated microtiter wells were washed three times with PBS. 500 ng of biotinylated anti-morphine M1 Fab was added into the wells in 100 µl of BSA/PBS and the wells were incubated for 30 min at RT on a shaker. After three PBS washes, sample dilutions spiked with morphine, amphetamine, tetrahydrocannabinol (THC) or S1 urine control were added into the wells in 50 µl of BSA/PBS. 1:100 diluted europium labelled K11 scFv was added into the wells in 50 µl of BSA/PBS and the incubation was continued for 1 h. Wells were washed three times with PBS and 100 µl of Enhancement solution (Wallac) was added into the wells. After 15-min shaking at RT, fluorescence was detected by VictorV fluorometer (Wallac). Results are shown in FIG. 2. There is a significant difference in affinity between the binding of K11 scFv to the primary antibody fragment M1 and to the M1 and morphine immune complex. This allows the detection of 1 ng/ml of morphine in a sample. No cross-reactivity with amphetamine or THC was detected.

A Homogenous Time Resolved Fluorescent Resonance Energy Transfer (TR-FRET)

The anti-morphine Fab fragment M1 was labelled with europium by the LANCE Eu-W1024 ITC chelate Kit (Wallac). The buffer of the labelled M1 was changed to 50 mM Tris, pH 7.8, 0.9% NaCl. The labelling yield was 1.1 Eu/Fab. The anti-M1+morphine immune complex scFv fragment K11 scFv was labelled with Cy5 by the FluoroLink-Ab Cy5 labelling kit (Amershampharmacia biotech). The labelling yield was 2 Cy5/scFv.

Figure 3:
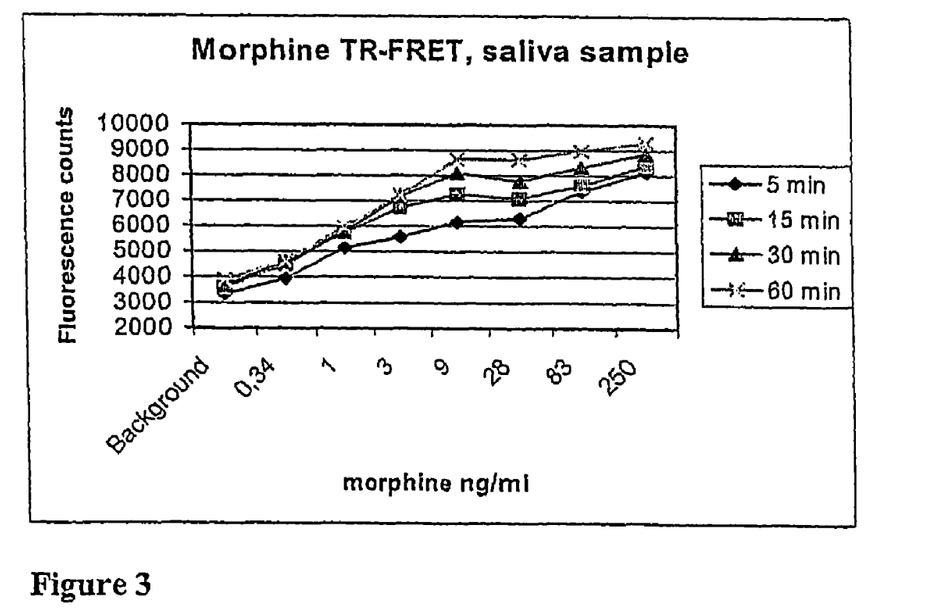
FIG. 3. A homogenous TR-FRET immunoassay of morphine.

Saliva was spiked with various dilutions of morphine and these samples were filtered through cotton wool before adding into the black microtiter wells (Nunc). 1 µg of europium labelled M1 Fab and 1 µg of Cy5 labelled K11 scFv was added into the wells in 50 µl of BSA/PBS. TR-FRET was read after 5, 15, 30, or 60 min incubation at RT by VictorV fluorometer (Wallac). Results are shown in FIG. 3. After five minutes incubation, 1 ng/ml of morphine in saliva was detected.

While one strategy for providing reagents and assays of the invention has been described, numerous variations and modifications will become apparent to the person skilled in the art.

EXAMPLE 2

Figure 4:
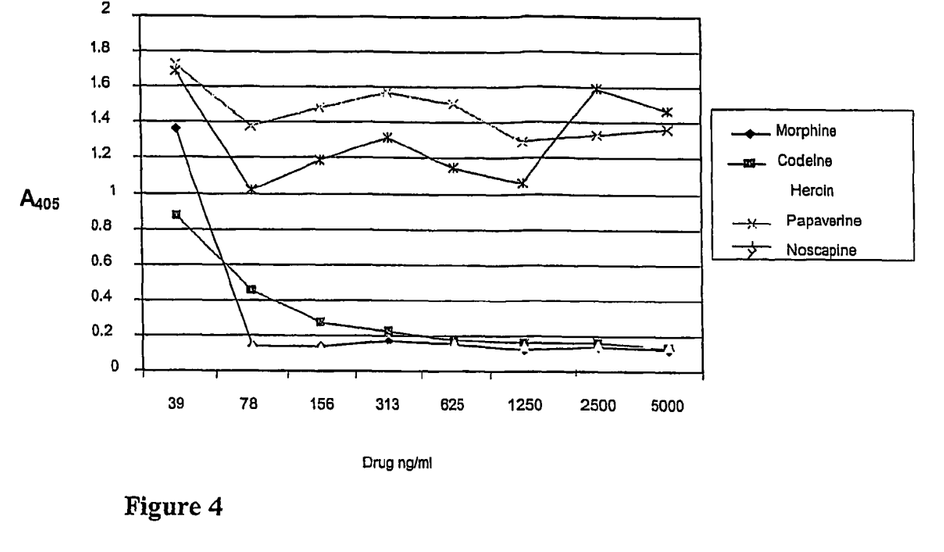
FIG. 4. Analysis of cross-reactivity of M1 anti-morphine Fab-fragment with codeine, heroin, noscapine and papaverine by a competitive ELISA.

Cross-reactivity of the M1 Fab-fragment with Codeine, Heroin, Noscapine and Papaverine Cross-reactivity of M1 anti-morphine Fab-fragment with codeine, heroin, noscapine and papaverine was tested in a competitive ELISA. Microtiter plate wells were coated o/n at +4° C. with 500 ng of morphine-BSA in 100 µl of Na-bicarbonate buffer, pH 9.8. The wells were washed three times with PBS and blocked with 0.5% BSA/PBS for 1 h at RT and washed again three times with PBS. Two parallel 100 µl samples containing morphine, codeine, heroin, noscapine or papaverine (39, 78, 156, 313, 625, 1250, 2500 or 5000 ng/ml) in PBS with 5 ng of purified M1 Fab were added into the wells and incubated for 30 min at RT on a shaker and washed three times with PBS. 1:2000 diluted alkaline phosphatase conjugated anti-Fab antibody (Sigma, A-1293) was added to the wells in 100 µl of 0.5% BSA/PBS and incubated for 30 min at RT on a shaker. Wells were washed three times with PBS, 100 µl of alkaline phosphatase substrate solution was added and $A_{405}$ was measured. The results are shown in FIG. 4. According to the competitive ELISA result M1 antibody has high cross-reactivity to codeine and heroin, which are structurally very similar with morphine.

A Homogenous Time Resolved Fluorescent Resonance Energy Transfer (TR-FRET) Imunoassay for Morphine The anti-morphine Fab fragment M1 was labelled with europium by LANCE Eu-W1024 ITC chelate Kit (Wallac). The buffer of the labelled M1 was changed to 50 mM Tris, pH 7.8, 0.9% NaCl. The labelling yield was 1.1 Eu/Fab. The anti-M1+morphine immune complex scFv fragment K11 was labelled with Cy5 by FluoroLink-Ab Cy5 labelling kit (Amersham Pharmacia Biotech). The labelling yield was 2 Cy5/scFv.

Figure 5:
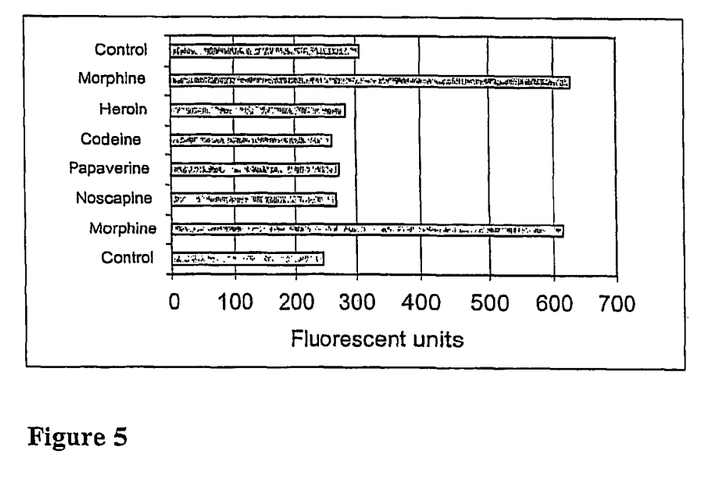
FIG. 5. A comparative TR-FRET based homogeneous immunoassay for morphine.

Saliva was spiked with a high concentration (10 µg/ml) of the following drugs: morphine, heroin, codeine, papaverine and noscapine. The samples were filtered through cotton wool before adding into black microtiter wells (Nunc). 1 µg of europium labelled M1 Fab and 1 µg of Cy5 labelled K11 scFv was added into the wells in 50 µl of BSA/PBS. As the control the background fluorescence from the M1 and K11 antibody pair without any added drug was measured. TR-FRET was read after 5 min incubation at RT by VictorV fluorometer (Wallac). The results are shown in FIG. 5.

Saliva sample spiked with morphine is giving a high fluorescent value, whereas the other drugs are giving fluorescent values that are similar to the background fluorescence detected from the control (labelled M1 and K11 scFv fragments without any added drug). K11 scFv binds the immune complex formed between M1 and mophine with extremely high specificity. K11 is able to discriminate completely M1 and morphine immune complex from the immune complexes between M1 and heroin or M1 and codeine, which gave fluorescent values corresponding to the background level.

REFERENCES

Barbas, C. F. III, Kang, A. S., Lerner, R. A., Benkovic, S. J. (1991) Assembly of combinatorial antibody libraries on phage surfaces: the gene III site. *Proc. Natl. Acad. Sci. USA* 88:7978-7982.

Hemmilä, I., Malminen, O., Mikola, H., Lbvgren, T. (1988) Homogeneous time-resolved fluoroimmunoassay of thyroxin in serum. *Clin. Chem.* 34:2320-2322.

Hoogenboom H. R., de Bruïne, A. P., Hufton, S. E., Hoet, R. M., Arends, J.-W., and Roovers, R. C. (1998) Review article: Antibody phage display technology and its applications. *Immunotechnology* 4, 1-20.

Kobayashi, N., Oiwa, H., Kubota, K., Sakoda, S., Goto, J. (2000) Monoclonal antibodies generated against an affinity-labeled immune complex of an anti-bile acid metabolite antibody: an approach to noncompetitive hapten immunoassays based on anti-idiotypic or anti-metatype antibodies. *J Immunol Methods,* 245, 95-108.

Kohler, G. and Milstein, C. (1975) Continuous cultures of fused cells secreting antibody of predefined specificity. *Nature,* 256, 495-7.

Mares, A., De Boever, J., Osher, J., Quiroga, S., Barnard, G. and Kohen, F. (1995) A direct non-competitive idiometric enzyme immunoassay for serum oestradiol. *J Immunol Methods,* 181, 83-90.

Maruyama, H., Sperlagh, M., Zaloudik, J., Liang, S., Mizuki, K., Molthoff, C. and Herlyn, D. (2002) Immunization procedures for anti-idiotypic antibody induction in mice and rats. *J Immunol Methods,* 264, 121.

Sambrook, J., Fritsch, E. F., and Maniatis, T. (1990) Molecular Cloning: A laboratory Manual, 2nd Ed., Cold Spring Horbor Laboratory Press, Cold Spring Harbor, N.Y.

Self, C. H., Dessi, J. L. and Winger, L. A. (1994) High-performance assays of small molecules: enhanced sensitivity, rapidity, and convenience demonstrated with a non-competitive immunometric anti-immune complex assay system for digoxin. *Clin Chem,* 40, 2035-41.

Suzuki, C., Ueda, H., Mahoney, W. and Nagamune, T. (2000) Open sandwich enzyme-linked immunosorbent assay for the quantitation of small haptens. *Anal Biochem,* 286, 238-46.

Suzuki, C., Ueda, H., Tsumoto, K., Mahoney, W. C., Kumagai, I. and Nagamune, T. (1999) Open sandwich ELISA with V(H)-/V(L)-alkaline phosphatase fusion proteins. *J Immunol Methods,* 224,171-84.

Szöllösi, J., Damjanovich, S., Mátyus, L. (1998) Application of Fluorescence Resonance Energy Transfer in the Clinical Laboratory: Routine and Research. *Communications in Clinical Cytometry,* 34:159-179.

Towbin, H., Motz, J., Oroszlan, P. and Zingel, O. (1995) Sandwich immunoassay for the hapten angiotensin II. A novel assay principle based on antibodies against immune complexes. *J Immunol Methods,* 181, 167-76.

Ueda, H., Tsumoto, K., Kubota, K., Suzuki, E., Nagamune, T., Nishimura, H., Schueler, P. A., Winter, G., Kumagai, I. and Mohoney, W. C. (1996) Open sandwich ELISA: a novel immunoassay based on the interchain interaction of antibody variable region. *Nat Biotechnol,* 14,1714-8.

Ullman, E. F., Milburn, G., Jelesko, J., Radika, K., Pirio, M., Kempe, T. and Skold, C. (1993) Anti-immune complex antibodies enhance affinity and specificity of primary antibodies. *Proc Natl Acad Sci USA,* 90, 1184-9.

Yokozeki, T., Ueda, H., Arai, R., Mahoney, W. and Nagamune, T. (2002) A homogeneous noncompetitive immunoassay for the detection of small haptens. *Anal Chem,* 74, 2500-4.

---

The invention claimed is:

1. A non-competitive immunoassay for detecting a small analyte, said assay comprising:

reacting a sample containing said analyte with a reagent pair comprising a first binding partner that binds to said analyte, and a second binding partner that binds to the complex of said analyte and said first binding partner, wherein said second binding partner is obtained from a non-immunized source which is a naive display recombinant binding partner library by selecting a binding partner that binds to said complex of the analyte and first binding partner, and determining the binding of the second binding partner, thus indicating the presence of the analyte in the sample, wherein the analyte has a molecular weight of less than 5000.

2. The assay of claim 1, wherein the first and second binding partners are selected from antibody fragments Fab and scFv.

3. The assay of claim 1, which assay is a homogeneous assay.

4. The assay of claim 3, which assay is based on fluorescence resonance energy transfer (FRET)

5. The assay of claim 1, wherein the analyte is a drug of abuse.

6. The assay of claim 5, wherein the analyte is morphine, tetrahydrocannabinol (THC) or amphetamine.

7. A non-competitive immunoassay for detecting a small analyte, said assay comprising:
reacting a sample containing said analyte with a reagent pair comprising a first binding partner that binds to said analyte, and a second binding partner that binds to the complex of said analyte and said first binding partner, wherein said second binding partner is obtained from a non-immunized source which is a naive display recombinant binding partner library by selecting a binding partner that binds to said complex of the analyte and first binding partner, and determining the binding of the second binding partner, thus indicating the presence of the analyte in the sample, wherein the analyte has a molecular weight of less than 5000, wherein the second binding partner comprises a ligand binding portion of K11 scFv comprising SEQ ID NO 5.

8. A non-competitive immunoassay for detecting a small analyte, said assay comprising:
reacting a sample containing said analyte with a reagent pair comprising a first binding partner that binds to said analyte, and a second binding partner that binds to the complex of said analyte and said first binding partner, wherein said second binding partner is obtained from a non-immunized source which is a naive display recombinant binding partner library by selecting a binding partner that binds to said complex of the analyte and first binding partner, and determining the binding of the second binding partner, thus indicating the presence of the analyte in the sample, wherein the analyte has a molecular weight of less than 5000, wherein the first binding partner comprises a ligand-binding portion of M1 Fab comprising SEQ ID NO 1 and SEQ ID NO 2, or of M2 Fab comprising SEQ ID NO 3 and SEQ ID NO 4.

9. The assay of claim 7, wherein the first binding partner comprises a ligand-binding portion of M1 Fab comprising SEQ ID NO 1 and SEQ ID NO 2, or of M2 Fab comprising SEQ ID NO 3 and SEQ ID NO 4.

10. The assay of claim 7, wherein said ligand-binding portion of the second binding partner is formed by amino acids no. 3 to 120 and no. 140 to 246 of SEQ ID NO 5.

11. The assay of claim 8, wherein said ligand-binding portion of the first binding partner is formed by amino acids no. 3 to 108 of SEQ ID NO 1 and amino acids no. 4 to 123 of SEQ ID NO 2; or of amino acids no. 3 to 108 of SEQ ID NO 3 and of amino acids no. 4 to 123 of SEQ ID NO 4.

12. The assay of claim 9, wherein said ligand-binding portion of the first binding partner is formed by amino acids no. 3 to 108 of SEQ ID NO 1 and amino acids no. 4 to 123 of SEQ ID NO 2; or of amino acids no. 3 to 108 of SEQ ID NO 3 and of amino acids no. 4 to 123 of SEQ ID NO 4.

13. The assay of claim 5, wherein multiple drugs of abuse are assayed.

* * * * *